United States Patent
Ruiz

[11] Patent Number: 5,976,174
[45] Date of Patent: Nov. 2, 1999

[54] MEDICAL HOLE CLOSURE DEVICE AND METHODS OF USE

[76] Inventor: Carlos E. Ruiz, 1747 N. Country La., Pasadena, Calif. 91107

[21] Appl. No.: 08/990,896

[22] Filed: Dec. 15, 1997

[51] Int. Cl.⁶ .................................................. A61B 17/04
[52] U.S. Cl. ............................................ 606/213; 606/151
[58] Field of Search ...................... 606/213, 215, 606/151, 153; 600/32

[56] References Cited

U.S. PATENT DOCUMENTS

| | | |
|---|---|---|
| 2,513,771 | 7/1950 | Williams . |
| 3,874,388 | 4/1975 | King et al. .............................. 128/334 |
| 4,031,569 | 6/1977 | Jacob ............................................... 3/1 |
| 4,917,089 | 4/1990 | Sideris .................................... 606/215 |
| 5,108,420 | 4/1992 | Marks ...................................... 606/213 |
| 5,192,301 | 3/1993 | Kamiya et al. .......................... 606/213 |
| 5,366,478 | 11/1994 | Brinkerhoff et al. ................... 606/213 |
| 5,425,744 | 6/1995 | Fagan et al. ............................. 606/213 |
| 5,578,045 | 11/1996 | Das ......................................... 606/151 |
| 5,861,003 | 1/1999 | Latson et al. ........................... 606/213 |

*Primary Examiner*—Michael H. Thaler
*Attorney, Agent, or Firm*—Fish & Neave; Nicola A. Pisano

[57] ABSTRACT

A hole closure device for use in medical applications, especially in treating cardiac septal defects, is provided that seals a hole by exerting pressure on an interior edge of the hole. The device includes a flexible tube that extends through a hole, and has an expansion ring disposed within it adjacent to the tissue on either side of the hole. The expansion rings, which have deployed diameters larger than that of the hole, cause the material of the tube in a mid-region of the tube to contact and conform to the interior edge of the hole. Methods for deploying the hole closure device to correct septal defects are also described.

20 Claims, 3 Drawing Sheets

MEDICAL HOLE CLOSURE DEVICE AND METHODS OF USE

FIELD OF THE INVENTION

The present invention relates to a system and method for closing holes in tissue, and in particular, for treating septal defects in the heart. More specifically, the invention relates to a device that is percutaneously inserted to deliver a device that seals a hole by expanding radially to contact the edges of the hole.

BACKGROUND OF THE INVENTION

Septal defects, holes in the septum dividing the right and left atria and right and left ventricles, are common congenital cardiac defects. Conventionally, such atrial and ventricular septal defects have been surgically corrected, requiring a thoracotomy and all of the attendant risks to the patient's health presented by open surgery.

In an attempt to overcome some of the risks attending surgical correction of septal defects, a number of percutaneously deliverable devices have been devised to seal cardiac septal defects. For example, U.S. Pat. No. 3,874,388 to King et al. describes a device comprising a pair of mechanically connected umbrella-like structures covered with a fluid impermeable material and having barbs that attach the device to the tissue surrounding the septal defect. The umbrella-like structures are closed for percutaneous delivery, and then expanded into position, one on either side of the tissue surrounding the defect, to close the hole.

U.S. Pat. No. 5,578,045 to Das, U.S. Pat. No. 5,192,301 to Kamiya et al., and U.S. Pat. No. 4,917,089 to Sideris all describe percutaneously medical hole closure devices having two closure members disposed on opposite sides of the hole and connected by a connecting member, such as a spring. These devices seek to seal a hole by holding the closure members tightly against the tissue adjacent to either side of the hole.

Previously known septal defect closure devices have a number of drawbacks. Foremost among these disadvantages is the inability of the devices to conform to the size of the septal defect. Such devices therefor require great care in placement, to ensure that the closure members entirely cover the hole. Because the previously known devices typically use expanding frames to support the closure members that can easily straddle the hole, or otherwise become caught, complications may arise during implantation of such devices.

Previously known devices also require that the closure members exert a high compressive contact force on either side of the tissue surrounding the hole. In many instances, there may be insufficient intact wall area surrounding the hole to permit placement of the closure members without interfering with other cardiac structures, such as the atrioventricular valves. The tissue surrounding a hole also may move, expand, or contract, during the cardiac cycle, making it difficult for the closure members to maintain a good seal, or the hole may deform over time.

In addition, the connecting member used to retain the closure members in intimate contact with the tissue surrounding the hole may experience stress relaxation and creep, phenomena whereby the connecting member loses its resiliency. The resulting loss in compressive contact force permits the closure members to leak. Previously known devices, such as described above, also present a risk of fatigue fracture under conditions commonly found in the heart.

It therefore would be desirable to provide apparatus and methods for percutaneously closing holes in the heart, and other tissue, in which the device conforms to the size of the hole.

It also would be desirable to provide apparatus and methods for percutaneously closing holes in the heart, and other tissue, in which the device may be easily deployed without complications associated with premature or mispositioned deployment of the closure members.

It further would be desirable to provide apparatus and methods for closing holes in the heart, and other tissue, which are able to seal a hole without requiring high compressive contact forces on tissue adjacent to the hole.

It yet further would be desirable to provide apparatus and methods for closing holes in the heart, and other tissue, which employ components that are not subjected to continual loading, and therefore present a low risk of leakage due to stress relaxation or fatigue fracture.

SUMMARY OF THE INVENTION

In view of the foregoing, it is an object of the present invention to provide apparatus and methods for percutaneously closing holes in the heart, and other tissue, in which the device conforms to the size of the hole.

It is another object of this invention to provide apparatus and methods for percutaneously closing holes in the heart, and other tissue, in which the device may be easily deployed without complications associated with premature or mispositioned deployment of the closure members.

It is a further object of the present invention to provide apparatus and methods for closing holes in the heart, and other tissue, which are able to seal a hole without requiring high compressive contact forces on the tissue adjacent to the hole.

It yet another object of the present invention to provide apparatus and methods for closing holes in the heart, and other tissue, which employ components that are not subjected to continual loading, and therefore present a low risk of leakage due to stress relaxation or fatigue fracture.

These and other objects of the present invention are achieved by providing a hole closure device and methods of use, that exerts a radial force against the edges of the hole, rather than requiring high compressive contact forces on tissue adjacent to the hole. In accordance with the present invention, the device comprises a flexible tube that is inserted through the hole and then radially expanded on either side of the hole. Expansion of the ends of the tube cause a mid-region of the tube to contact and conform to the dimensions of the hole, and to exert a radial force along the edge of the hole, thereby sealing it.

In a preferred embodiment, the ends of the tube are radially expanded using shape-memory elements, which may be transluminally inserted in a contracted delivery state and then released to resume an expanded deployed state. In other embodiments, the ends of the tube may be expanded using inflatable members.

Methods for implanting a device constructed in accordance with the present invention correct septal defects are also provided.

BRIEF DESCRIPTION OF THE DRAWINGS

Further features of the invention, its nature, and various advantages will be more apparent from the accompanying drawings and the following detailed description of the preferred embodiments, in which.

DETAILED DESCRIPTION OF THE INVENTION

The present invention seals large diameter holes, such as atrial and ventricular septal defects, by providing a hole closure device that contacts and conforms to an interior edge of the hole. Unlike previously known hole closure devices, the present invention does not require high compressive contact forces on the lateral faces of the tissue adjacent to the hole to prevent leakage. Accordingly, the hole closure device of the present invention is less prone to mechanical fatigue or stress-relaxation failure. In addition, the hole closure device of the present invention is far simpler in construction than many previously known devices, and thus less prone to the deployment complications that may occur with previously known devices.

Figure 1A:
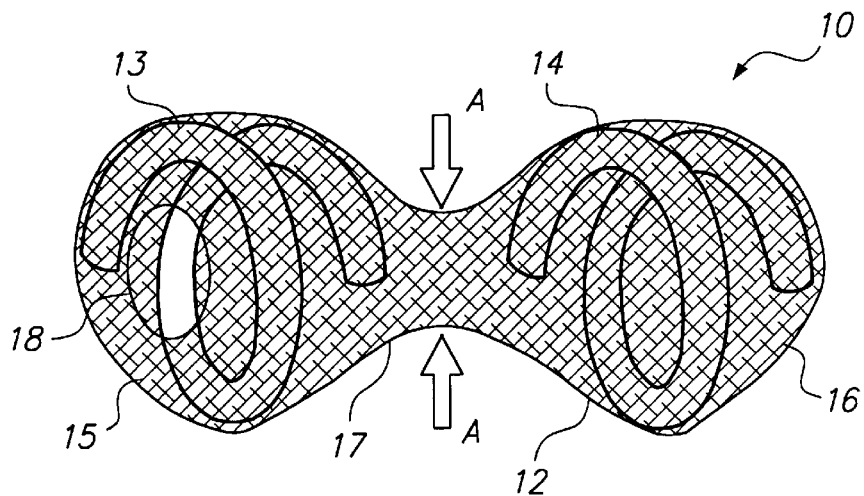
FIGS. 1A and 1B are, respectively, a perspective and side view of an illustrative embodiment of the device of the present invention disposed in septal defect.
Figure 1B:
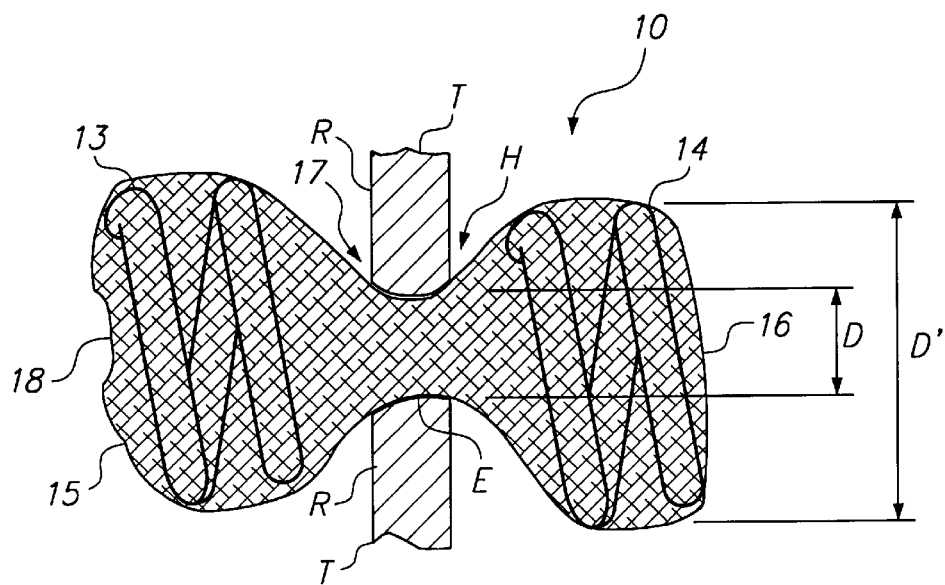

Referring to FIGS. 1A and 1B, hole closure device 10 constructed in accordance with the principles of the present invention is described. Device 10 illustratively comprises flexible tube 12 having expansion rings 13 and 14 disposed at proximal end 15 and distal end 16. Expansion rings 13 and 14 cause proximal end 15 and distal end 16, respectively, of tube 12 to flare radially outward, thereby urging mid-region 17 of tube 12 to engage the interior edge of a hole (indicated by arrows A in FIG. 1A).

When deployed, distal end 16 of tube 12 is located on the one side of the hole, while proximal end 15 is located on the other side of the hole, as in previously known hole closure devices. As depicted in FIG. 1B, however, hole closure device 10 seals hole H in tissue T by exerting pressure radially against the surface of edge E of the hole, rather than against regions R adjacent to the hole, as in previously known devices. Expansion rings 13 and 14 are configured to be larger than the diameter D of hole H when deployed, so that mid-region 17 tube 12 expands radially outward and contacts and conforms to the shape of hole H.

Because tube 12 is constructed from a flexible material, it is capable of moving, expanding and contracting to accommodate changes in the size and shape of hole H as the heart contracts. In addition, because expansion rings 13 and 14 are larger than diameter D of hole H in their deployed state, mid-region 17 of tube 12 will continuously remain in contact with edge E of the hole and prevent leakage.

Tube 12 preferably comprises a flexible biocompatible material typically used in arterial grafts, such as a polyester fiber (e.g., Dacron®, a registered trademark of E.I. duPont de Nemours, Wilmington, Del.), polytetrafluoroethylene (PTFE), or nylon. Proximal end 15 of tube 12 includes opening 18 through which the delivery catheter deploys expansion rings 13 and 14 within the tube, while distal end 16 of tube 12 is sewn or sutured closed.

Expansion rings 13 and 14 have a deployed diameter D' greater than that of hole H. When deployed in tube 12, the expansion rings stretch the material of tube 12 to conform to the deployed shape of the expansion rings. This in turn causes mid-region 17 of tube 12 to expand radially outward to engage and conform to the perimeter of the hole.

Expansion rings 13 and 14 illustratively comprise coil loops of a shape-memory alloy or polymer, for example, nickel-titanium, and may have a shape-memory property which is either mechanically or thermally activated. The coil loops may be circular or elliptical, and may form a single open ring or a multi-turn helix, so long as the diameter of the coil loop is larger than the hole which is to be sealed. Stated another way, the circumference of the expansion rings, when deployed, must be larger than the perimeter of the hole. Expansion rings 13 and 14 preferably are coated with a radioopaque material, so that they are visible under a fluoroscope.

Figure 2:
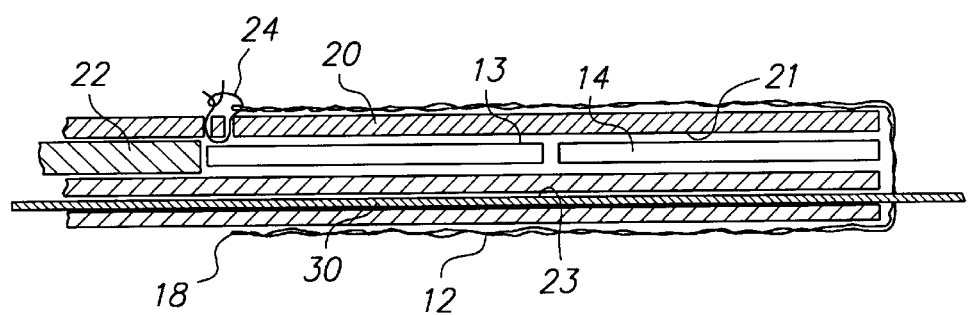
FIG. 2 is a partial sectional view of the hole closure device of FIG. 1 disposed in a delivery catheter.

In FIG. 2, expansion rings 13 and 14 are shown in their delivery state, in which the rings are uncoiled to form straight wire segments suitable for insertion in lumen 21 of delivery catheter 20. When ejected from lumen 21 by push rod 22, expansion rings 13 and 14 transition to their deployed state, as shown in FIGS. 1A and 1B, in which the rings assume a coiled shape.

In one embodiment, expansion rings 13 and 14 undergo the transition from the delivery state to the deployed state as a result of being released from a constrained position, as described, for example, in U.S. Pat. No. 5,067,957 to Jervis, which is incorporated herein by reference. Alternatively, expansion rings 13 and 14 may undergo the transition from delivery to deployed states as a result of being exposed to body temperature, as described, for example, in U.S. Pat. No. 4,512,338 to Balko, which is incorporated herein by reference.

Referring again to FIG. 2, a distal end of delivery catheter 20 for delivering hole closure device 10 of FIG. 1 is described. Delivery catheter 20 includes lumen 21 having push-rod 22 slidingly disposed therein for movement in the proximal and distal directions, and guide wire lumen 23. Catheter 20 comprises a flexible material typically employed in catheter construction, such as polyvinyl chloride or polyethylene. Guide wire lumen 23 accepts guide wire 30 to transluminally guide the delivery device to a deployment site.

Expansion rings 13 and 14 are uncoiled and inserted within lumen 21 of catheter 20 in abutting end-to-end relation, so that the proximal end of expansion ring 13 abuts against push rod 22. Catheter 20 is then inserted through opening 18 in tube 12, and tube 12 is slipped over the exterior of catheter 20 in the proximal direction. Lightweight suture 24 may be placed through tube 12 to retain the tube in position on catheter 20 until the hole closure device is deployed.

With respect to FIGS. 3A–3D, methods for deploying hole closure device 10 of the present invention are described for sealing a ventricular septal defect. As will be apparent from the following description, these methods may be readily adapted for correcting holes resulting from any of a number of defects, such as atrial septal defects, patent ductus arteriosus, aortopulmonary windows, Fontan fenestrations, post-operative residual patch leaks, or other conditions which require that a hole in the cardiovascular system be closed.

Figure 3A:
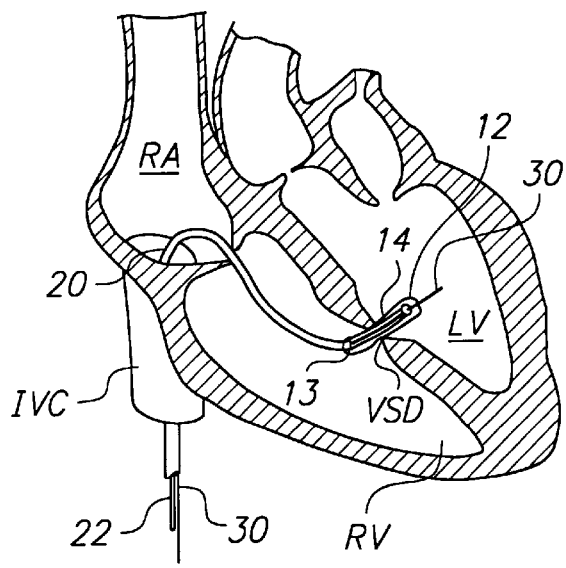
FIGS. 3A–3D are views showing the steps of deploying the device of FIG. 1 in accordance with the methods of the present invention to correct a ventricular septal defect.

In FIG. 3A, catheter 20 is advanced along guide wire 30 previously percutaneously and transluminally inserted via a femoral vein, inferior vena cava IVC, right atrium RA and right ventricle RV into ventricular septal defect VSD. In particular, catheter 20 is positioned, for example, under fluoroscopic guidance, so that the end of catheter 20 extends through ventricular septal defect VSD into left ventricle LV.

Figure 3B:
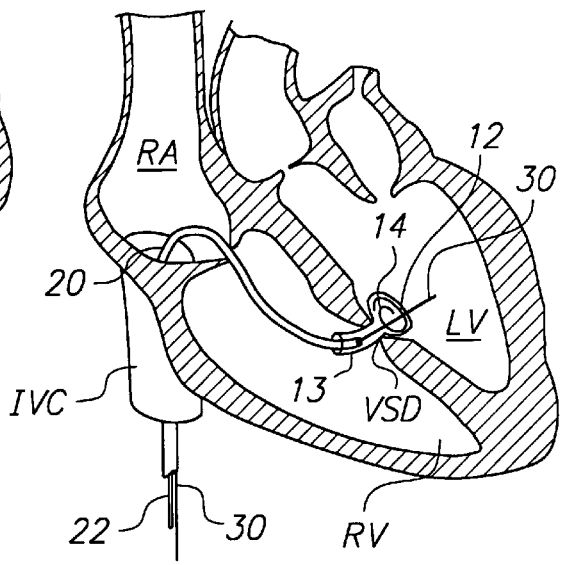

Once catheter 20 is positioned so that it extends across defect VSD, the clinician advances the proximal end of push rod 22 in the distal direction, thereby pushing expansion ring 14 out of lumen 21. As expansion ring 14 exits lumen 21, it transitions to its expanded deployed state, as described hereinabove with respect to FIG. 1. As shown in FIG. 3B, when expansion ring 14 deploys, it forms a coil inside distal end 16 of tube 12 that is larger than the diameter of defect VSD. Expansion ring 14 therefore stretches the material of distal end 16 of tube 12 to expand radially outward and conform to the deployed shape of the expansion ring.

Figure 3C:
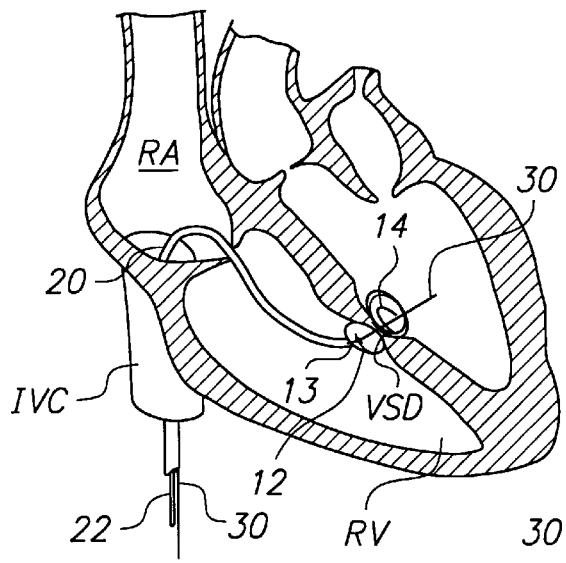

In FIG. 3C, the distal end of catheter 20 is shown withdrawn and disposed in right ventricle RV. Push rod 22 is then urged in the distal direction to push expansion ring 13 out of lumen 21. When expansion ring 13 is ejected, it transitions to its deployed state and forms a coil in proximal end 15 of tube 12 that stretches the material of proximal end 15 to conform to the shape of the expansion ring. Deployment of expansion rings 13 and 14 in tube 12 causes mid-region 17 to expand and contact the interior edge of the defect. Because the expansion rings continuously apply a radially outwardly directed load to the interior of tube 12, mid-region 17 continuously maintains contact with the perimeter of defect VSD, even if the tissue moves or the hole gradually changes shape.

Figure 3D:
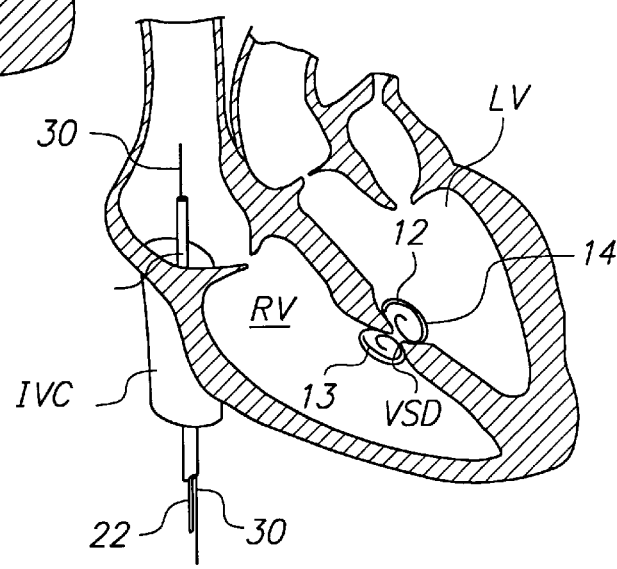

With respect to FIG. 3D, catheter 20 is withdrawn proximally, causing suture 24 to break and detaching tube 12 from the distal end of the catheter. The distal end of catheter 20 is then fully withdrawn through opening 18 in proximal end 15 of tube 12, and catheter 20 and guide wire 30 are removed.

It will be evident to one skilled in the art that variations of the foregoing procedure may be readily made. For example, septal defect could be reached by routing catheter 20 through the right internal jugular vein (or right subclavian vein) and the superior vena cava. In addition, the expansion rings could be advanced through lumen 21 after the catheter is in place, rather than being preplaced as shown in FIG. 2.

Tube 12 also may include a purse string disposed surrounding opening 18 in proximal end 15 of the tube. Tension may be exerted on this purse string to cause tube 12 to close, and to adjust the radial pressure exerted by mid-region 17 of the tube to insure that satisfactory sealing of the defect is achieved. Alternatively, other methods of tensioning and sealing tube 12 may be used. For example, a locking metal ring (not shown) may be disposed on the distal end of catheter 20 and dislodged to close opening 18 in proximal end 15 of tube 12.

It is expected that the flexible material comprising tube 12 will be substantially fluid impermeable. Accordingly, the presence of opening 18 in proximal end 15 of device 10, as well as any puncture in distal end 16 caused by guide wire 30, will result in very little leakage through the device.

In addition, after deployment of device 10 within a defect, push rod 22 may be withdrawn proximally and a suitable molding agent may be injected into the interior of tube 12. When the molding agent cures, it forms in-situ a fluid impermeable plug. Suitable molding agents may include fibrin separated from the patient's blood, collagen-based products, available from Collatec, Inc., Plainsboro, N.J., a starch-based polyethylene glycol hydrogel, available from Gel Med, Inc., Bedford, Mass., or poly-capro-lactone.

Figure 4:
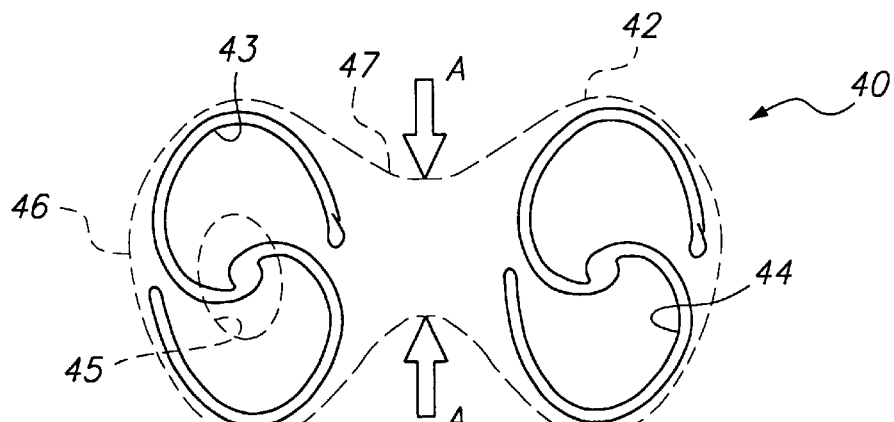
FIGS. 4–6 are, respectively, perspective views, partly in section, of alternative embodiments of the hole closure device of the present invention.
Figure 5:
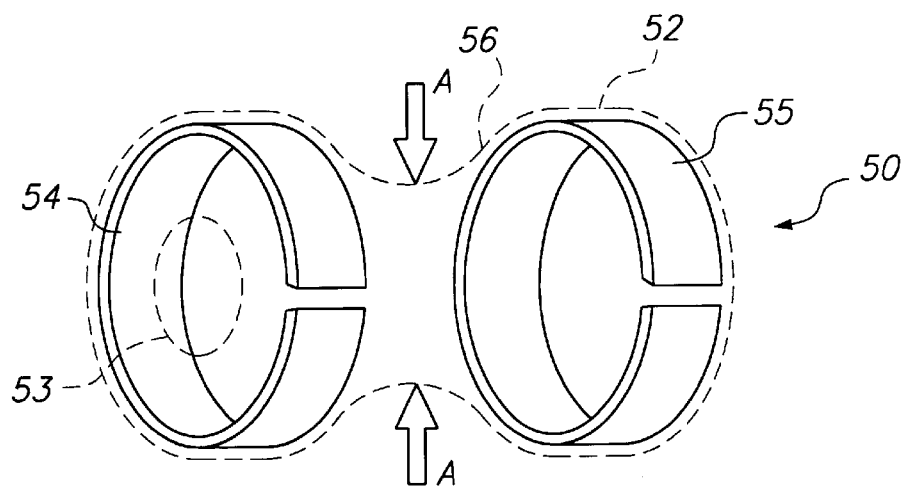
Figure 6:
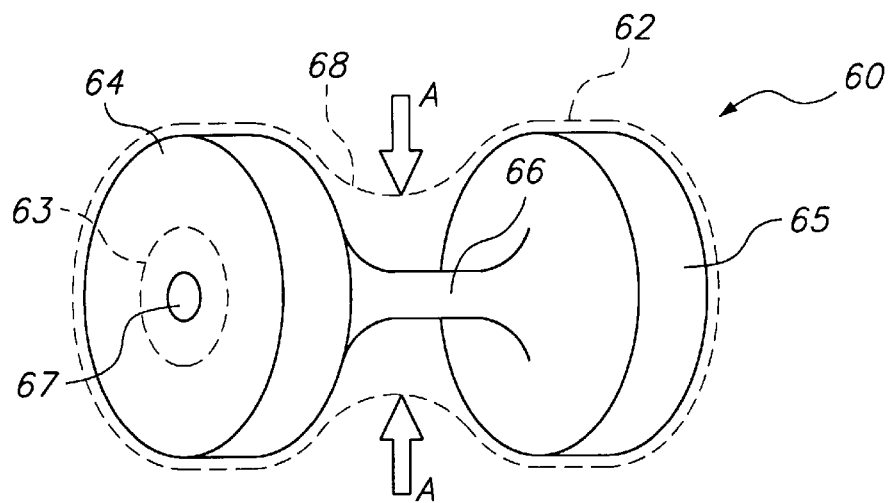

Referring now to FIGS. 4–6, alternative embodiments of hole closure devices constructed in accordance with the principles of the present invention are described. In FIGS. 4–6, the tubes forming the exterior of the closure devices are shown only in dotted line, so that the structure of the enclosed expansion rings may be clearly illustrated. In each of the devices of FIGS. 4–6, deployment of the expansion rings causes the mid-region of the tube to contact and conform to the tissue, indicated by arrows A.

In FIG. 4, hole closure device 40 comprises flexible tube 42 enclosing expansion rings in the form of spiral-shaped wire springs 43 and 44. Tube 42 includes opening 45 in proximal end 46 for permitting an insertion catheter to be disposed within tube 42 for delivery of the expansion rings. Tube 42 is constructed as described hereinabove for the embodiment of FIG. 1, while spiral springs 43 and 44 may comprise a resilient or shape memory metal alloy or polymer. As for the embodiment of FIG. 1, spiral springs 43 and 44 have a contracted delivery state, in which they may be loaded into a delivery catheter, and a deployed state, as illustrated in FIG. 4. Deployment of spiral springs 43 and 44 causes mid-region 47 of tube 42 to contact and conform to an interior edge of the hole, as described hereinabove.

In device 50 of FIG. 5, tube 52 having opening 53 encloses expansion rings having the form of narrow bands 54 and 55. Bands 54 and 55 preferably have a rectangular cross section, and may be wound down to a contracted delivery diameter for insertion into a catheter similar to catheter 20 of FIG. 2. Tube 52 and narrow bands 54 and 55 comprise similar materials to the corresponding components described hereinabove. Deployment of narrow bands 54 and 55 causes mid-region 56 of tube 52 to contact and conform to an interior edge of the hole, thus sealing the hole. Narrow bands 54 and 55 are shown as circular in shape, although they may comprise any suitable self-expanding shape, and may take the form of any type of polygon.

In device 60 of FIG. 6, flexible tube 62 having opening 63 encloses expansion rings comprising inflatable members 64 and 65. Inflatable members 64 and 65 are disposed at either end of tube 62 and are interconnected by inflation lumen 66 to inflation port 67. Inflation member 64 is detachable coupled to a push-rod within the delivery catheter, which push-rod includes an inflation lumen for injecting a suitable inflation medium into inflatable members 64 and 65. Device 60 is deployed in a manner similar to that of device 10 of FIG. 1.

In particular, inflatable members 64 and 65, connected by inflation lumen 66, are deflated and disposed within the lumen of a delivery catheter. Tube 62 is disposed on the exterior of the catheter as in FIG. 2. Once the catheter is positioned within the hole of the defect, a biocompatible inflation medium, such as saline solution, is injected via inflation port 67 and inflation lumen 66 to inflate inflatable member 65 within the left ventricle. Inflatable member 64 is then deployed from the catheter in the right ventricle, and inflated with inflation medium injected via inflation port 67. The catheter is then disconnected from inflation port 67 and removed. As illustrated in FIG. 6, inflation of inflatable members 64 and 65 causes mid-region 68 of tube 62 to contact and conform to the perimeter of the hole in the tissue, indicated by arrows A.

While preferred embodiments of the present invention are described above, it will be evident to one skilled in the art that various changes and modifications may be made to the devices and methods disclosed without departing from the invention. It is intended in the appended claims to cover all such changes and modifications which fall within the true spirit and scope of the invention.

What is claimed is:

1. Apparatus for use in medical applications to close a hole extending between a first tissue surface and a second tissue surface, the hole having a diameter and an interior edge, the apparatus comprising:

a tube having a distal end adapted to be disposed adjacent the first tissue surface, a proximal end adapted to be disposed adjacent the second tissue surface, and a mid-region adapted to be extended through the hole, the tube comprising a flexible material;

a first expansion ring disposed in the distal end of the tube, the first expansion ring having a deployed diameter greater than the diameter of the hole, the first expansion ring causing the flexible material at the distal end of the tube to conform to the deployed diameter of the first expansion ring; and a second expansion ring disposed in the proximal end of the tube, the second expansion ring having a deployed diameter greater than the diameter of the hole, the second expansion ring causing the flexible material at the proximal end of the tube to conform to the deployed diameter of the second expansion ring, wherein the first and second expansion rings are adapted to force the mid-region of the tube radially outward to contact and conform to the interior edge of the hole to seal the hole, without the first and second expansion rings or the tube applying a clamping force to the first and second tissue surfaces.

2. The apparatus as defined in claim 1, wherein the first and second expansion rings have a contracted delivery state for transluminal delivery.

3. The apparatus as defined in claim 1, wherein the first and second expansion rings comprise a shape memory material.

4. The apparatus as defined in claim 3, wherein the first and second expansion rings comprise, in an expanded deployed state, a coil.

5. The apparatus as defined in claim 2, wherein the first and second expansion rings comprise inflatable members.

6. The apparatus as defined in claim 4, wherein the coil comprises a nickel titanium alloy.

7. The apparatus as defined in claim 6, wherein the first and second expansion rings comprise, in the contracted delivery state, straight lengths of wire.

8. Apparatus for use in medical applications to close a hole extending between a first tissue surface and a second tissue surface, the hole having a perimeter and an interior edge, the apparatus comprising:

a tube having a distal end adapted to be disposed adjacent the first tissue surface, a proximal end adapted to be disposed adjacent the second tissue surface, and a mid-region adapted to be extended through the hole, the tube comprising a flexible material;

a first expansion member disposed in the distal end of the tube, the first expansion member having a deployed circumference greater than the perimeter of the hole, the first expansion member urging the flexible material at the distal end of the tube radially outward; and a second expansion member disposed in the proximal end of the tube, the second expansion member having a deployed circumference greater than the perimeter of the hole, the second expansion member urging the flexible material at the proximal end of the tube radially outward, wherein the first and second expansion members are adapted to force the mid-region of the tube radially outward to contact and conform to the interior edge of the hole to seal the hole, without the first and second expansion members or the tube applying a clamping force to the first and second tissue surfaces.

9. The apparatus as defined in claim 8, wherein the first and second expansion members have a contracted delivery state for transluminal delivery.

10. The apparatus as defined in claim 8, wherein the first and second expansion members comprise a shape memory material.

11. The apparatus as defined in claim 8, wherein the first and second expansion members comprise, in an expanded deployed state, a coil.

12. The apparatus as defined in claim 9, wherein the first and second expansion members comprise inflatable members.

13. The apparatus as defined in claim 10, wherein the coil comprises a nickel titanium alloy.

14. The apparatus as defined in claim 13, wherein the first and second expansion members comprise, in the contracted delivery state, straight lengths of wire.

15. A method for closing a hole in tissue, the hole extending between a first tissue surface and a second tissue surface, the hole having a perimeter and an interior edge, the method comprising steps of:

providing a tube of flexible material having proximal and distal ends;

inserting the tube within the hole so that the distal end is adjacent to the first tissue surface and the proximal end is adjacent to the second tissue surface;

inserting a first expansion ring into the distal end of the tube;

expanding the first expansion ring within the distal end of the tube to a deployed circumference greater than the perimeter of the hole;

inserting a second expansion ring into the proximal end of the tube; and expanding the second expansion ring within the proximal end of the tube to a deployed circumference greater than the perimeter of the hole, the step of expanding the second expansion ring causing a mid-region of the tube to contact and conform to the interior edge of the hole, without the first and second expansion rings or the tube applying a clamping force to the first and second tissue surfaces.

16. The method as defined in claim 15 wherein the steps of inserting the tube and inserting the first and second expansion rings are performed percutaneously.

17. The method as defined in claim 15 wherein the steps of expanding the first and second expansion rings comprise releasing a mechanical constraint from the first and second expansion rings.

18. The method as defined in claim 17 wherein the steps of releasing a mechanical constraint from the first and second expansion rings comprise ejecting the first and second expansion rings from the interior of a delivery catheter.

19. The method as defined in claim 15 wherein the steps of expanding the first and second expansion rings comprise exposing the first and second expansion rings to a temperature change that induces a transition in a shape-memory behavior of the first and second expansion rings.

20. The method as defined in claim 15 wherein the steps of expanding the first and second expansion rings comprise a step of injecting an inflation medium into the first and second expansion rings.

* * * * *